(12) United States Patent
Hertz

(10) Patent No.: US 8,882,507 B2
(45) Date of Patent: Nov. 11, 2014

(54) DENTAL IMPLANT AND METHOD OF USE WITH IMPROVED MAXILLARY STABILITY

(71) Applicant: Paul Hertz, Riverdale, NY (US)

(72) Inventor: Paul Hertz, Riverdale, NY (US)

( * ) Notice: Subject to any disclaimer, the term of this patent is extended or adjusted under 35 U.S.C. 154(b) by 0 days.

(21) Appl. No.: 13/947,006

(22) Filed: Jul. 19, 2013

(65) Prior Publication Data

US 2014/0023991 A1    Jan. 23, 2014

Related U.S. Application Data

(60) Provisional application No. 61/674,336, filed on Jul. 21, 2012.

(51) Int. Cl.
*A61C 8/00* (2006.01)
*A61K 6/04* (2006.01)
*A61C 8/02* (2006.01)

(52) U.S. Cl.
CPC .............. *A61C 8/0009* (2013.01); *A61C 8/0039* (2013.01); *A61C 8/0028* (2013.01); *A61C 8/0024* (2013.01); *A61K 6/04* (2013.01); *A61C 8/0092* (2013.01); *A61C 8/0006* (2013.01)
USPC ........................................................ 433/173

(58) Field of Classification Search
CPC ............................ A61C 8/0006; A61C 8/0004
USPC ........................................................... 433/173
See application file for complete search history.

(56) References Cited

U.S. PATENT DOCUMENTS

| | | | | |
|---|---|---|---|---|
| 5,547,378 | A | * | 8/1996 | Linkow .......................... 433/173 |
| 6,042,380 | A | * | 3/2000 | De Rowe ....................... 433/173 |
| 6,758,673 | B2 | * | 7/2004 | Fromovich et al. ............ 433/215 |
| 7,632,280 | B2 | * | 12/2009 | Hochman ........................ 606/94 |
| 7,934,929 | B2 | * | 5/2011 | Better et al. ................... 433/174 |
| 8,029,284 | B2 | | 10/2011 | Better et al. |
| 8,226,409 | B1 | * | 7/2012 | Karapetyan ................... 433/173 |
| 8,388,343 | B2 | | 3/2013 | Better et al. |
| 2007/0156251 | A1 | * | 7/2007 | Karmon ...................... 623/23.61 |
| 2009/0181345 | A1 | * | 7/2009 | Kfir ............................... 433/172 |
| 2010/0094329 | A1 | * | 4/2010 | Cardoso et al. ............... 606/192 |
| 2011/0039232 | A1 | * | 2/2011 | Yu ................................. 433/173 |
| 2011/0112512 | A1 | * | 5/2011 | Muni et al. .................... 604/514 |

FOREIGN PATENT DOCUMENTS

DE    43 21 785 C1  *  3/1995
DE    101 29 948 B4  *  11/2012

* cited by examiner

*Primary Examiner* — Ralph Lewis
(74) *Attorney, Agent, or Firm* — Kenneth B. Pickle, Esq.

(57) ABSTRACT

A dental implant apparatus and method of use which has a central conduit and a plurality of apical apertures through which fluid bone-grafting material may be extruded. A resorbable membrane surrounds the apical end of the apparatus and unfurls as bone-grafting material exits the apertures, thereby holding the fluid in close proximity to the implant.

8 Claims, 5 Drawing Sheets

DENTAL IMPLANT AND METHOD OF USE WITH IMPROVED MAXILLARY STABILITY

CROSS-REFERENCES

This patent application depends for priority on Provisional Application 61/674,336 filed on Jul. 21, 2012. This application is incorporated herein by reference, but is not admitted to be prior art with respect to the present invention by its mention in the background.

BACKGROUND

Osseointegrated implants are typically metallic screws that may be placed in a bone of a patient for supporting a prosthesis. For example, an osseointegrated implant may include a dental implant for insertion into a jawbone of a patient. Such an implant may support an artificial tooth after the loss of a natural tooth. Replacement of a tooth is often a challenging surgical procedure when the remaining bone has insufficient height to support the implant.

The success of implant dentistry in the maxillary posterior is determined largely by the available bone and the location of the sinus. Because maxillary bone is often soft and in short supply, it is generally helpful to use a regenerative material—such as autogenic, allogeneic, xenogeneic, or synthetic bone graft—to achieve additional bone mass, and thus, primary stability in the maxillary bone. Significant considerations in treatment include how posterior the edentulous area is, as well as the length of time a space has been edentulous.

Sinus lift surgery can restore, replace, and create bone in areas with inadequate bone. The procedure to place the grafts are often complicated, time consuming, invasive, painful, and expensive. A patient must have the additional surgery, and then wait 4-6 months until the graft has "taken" before the implant can be placed. The grafting procedure is also susceptible to infection; it can be uncomfortable; and it can be prohibitively expensive for patients.

Various dental implants and techniques have been developed to augment bones. One such technique includes a method of lifting a membrane using hydraulic pressure applied by a syringe. Another technique requires the use of various sinus burs and condensers of increasing width in conjunction with a pliable atraumatic bone grafting mixture and hydraulic pressure from a surgical handpiece. Another technique includes the use of a sleeve to raise the subantral membrane and form a cavity for injection of bone growth stimulant.

U.S. Pat. No. 8,388,343 to Better et al. attempted to overcome these deficiencies through the injection of bone grafting material through a hollow in the implant itself This injection occurs through an inlet on one side of the anchor, and takes place only during or prior to final placement of the anchor. This technique creates difficulty in getting the side inlet aligned with the tubing for the injection of bone grafting material. The implant described in Better et al. also fails to provide any means of holding the injected bone grafting material in place in close proximity to the implant, for further stability.

Although the above techniques may improve the ability to augment a bone, they have continuing deficiencies, including complexity, invasiveness, and pain. The dental implant system described herein can help reduce the need for sinus lift surgery, along with all the negatives associated with it. It avoids the high cost and high radiation exposure of a CT scan. It can achieve ideal implant placement using stock abutments rather than custom abutments. It need not be used only by very experienced specialists in the maxillofacial surgery field. All these positives lead to less cost to the patient, shorter treatment time, and greater ease of care for the dentist. Short implants and narrow implants—along with their inherent liabilities—can be avoided. Compared to current state-of-the-art dental-implant-bone-grafting techniques, the dental implant system described herein provides a reduction of steps, easier bone-grafting material extrusion post-graft, more secure grafts, and decreased need for sinus lift surgery.

SUMMARY

The present invention is directed generally to dental implants and implantation methods, and specifically to implants and implantation methods that reduce the need for sinus lift surgery.

In some embodiments, an apparatus includes a dental implant with an apical end and a coronal end. The apparatus may further include a conduit extending through the implant with at least one outlet aperture towards the apical implant end. The conduit may also include an inlet opening at the coronal end of the implant. Further, the inlet opening, the conduit, and the outlet aperture may be configured for implantation in a bone such that when fully implanted, the inlet opening remains open to receiving fluid bone-grafting material.

In some embodiments, a resorbable barrier membrane may surround the implant such that the extrusion of fluid through the outlet aperture causes the membrane to unfurl and hold the fluid in place in close proximity to the implant.

In some embodiments, a dowel pin may be provided within the conduit, connected to the membrane, and configured to slide apically along the conduit as bone-grafting material is extruded, thereby aiding in the membrane unfurling.

In further disclosed embodiments, an implant method includes providing a dental implant shaped so as to define a conduit threrethrough, having at least one aperture towards the apical end, a means for extruding fluid through the aperture(s), and a membrane surrounding the apical end, configured to unfurl as fluid is extruded from the aperture(s); drilling or boring a hole into maxillary bone; inserting the implant into the hole; and injecting fluid bone-grafting material into the conduit to unfurl the membrane, keeping the material close to the implant while it hardens to aid in primary stability.

In one exemplary embodiment, the apical half of the implant is about 0.7 mm narrower than the coronal half The coronal half may be similar to many existing platform bodies, and may be self-tapping surgical grade titanium. The implant body may be secondarily wrapped in a resorbable membrane film. The shape of the implant may be roughly conical, and may use the internal hex design.

One exemplary embodiment may contain a circumferential protrusion 2 mms apically to the end of the implant's internal screw junction to allow for the graft material canula to push past so that the liquefied bone grafting material may then be injected into the implant and out through the porthole outlets.

These and other features, aspects, and advantages of the present invention will become better understood with regard to the following description, appended claims, and accompanying drawings. It is to be understood that the foregoing summary addresses only a few exemplary aspects of the invention, and that both the foregoing general description and the following detailed description are exemplary and explanatory only and are not restrictive of the invention as claimed.

DESCRIPTION

Figure 1:
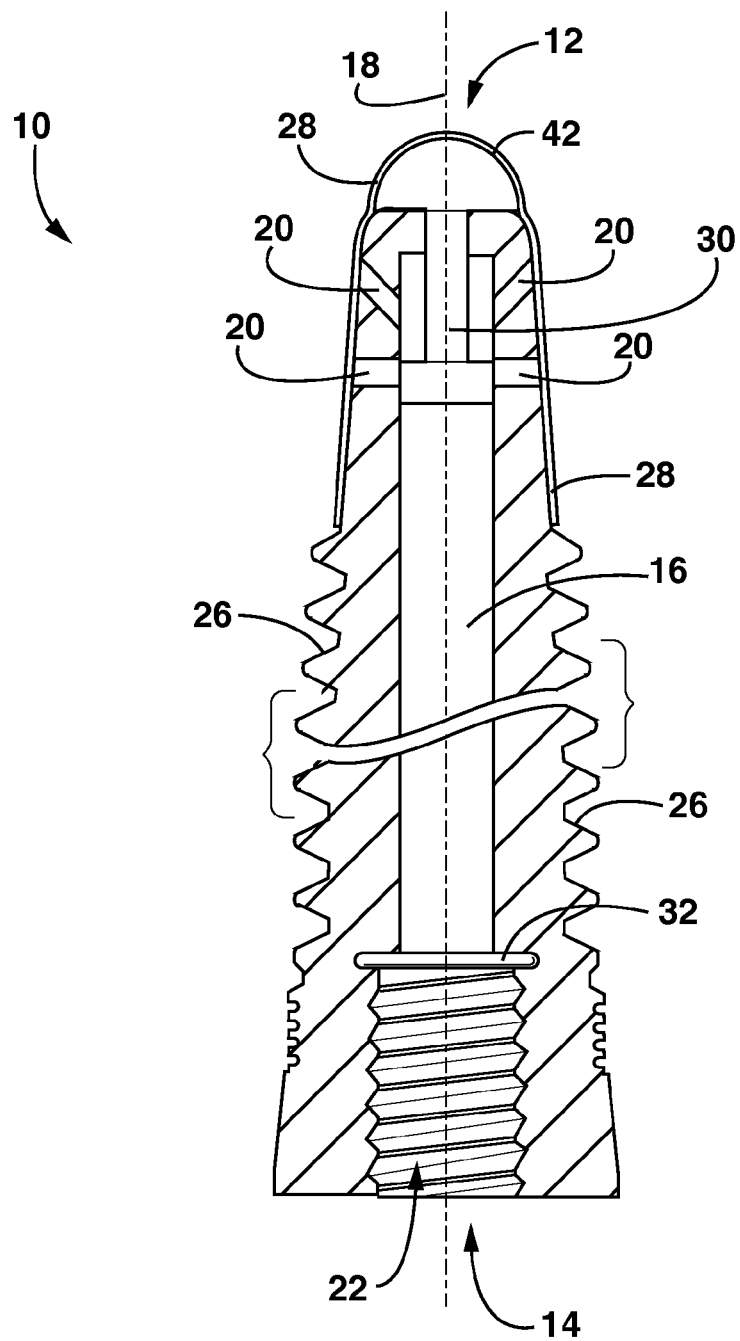
FIG. 1 is a section view taken from FIG. 2.
Figure 2:
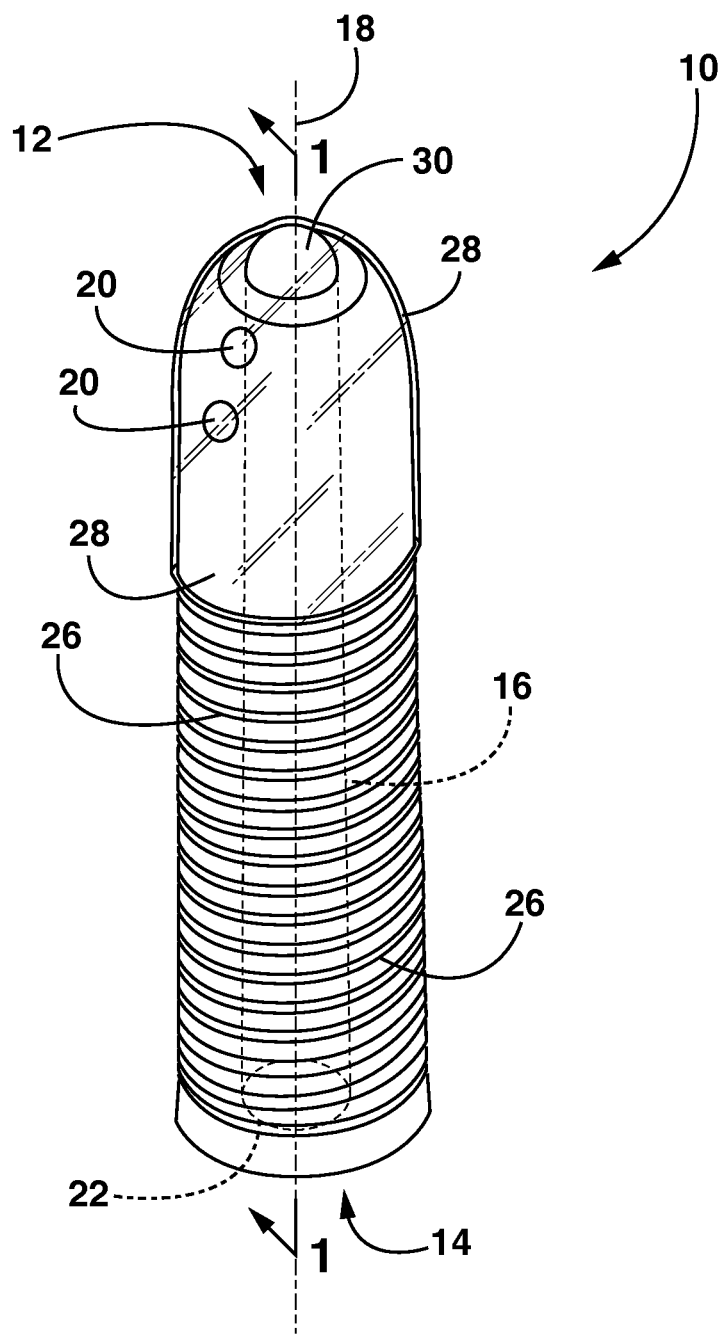
FIG. 2 is a perspective view of the dental implant.

FIG. 1 is a schematic illustration of a dental implant apparatus in accordance with an embodiment of the present invention. The apparatus comprises a dental implant 10, shaped so as to define a conduit 16 therethrough. Implant 10 has an apical end 12 and a coronal end 14, and at least one aperture 20 towards the apical end 12. Some embodiments of the dental implant 10 may be 10 mm or 12 mm long and 5 mm or 6 mm wide. The shape of implant 10 may be roughly conical, and the apical portion 12 may be about 0.7 mm narrower than the coronal portion 14. In one embodiment, coronal portion 14 may be made of self-tapping surgical grade titanium.

Internal to coronal portion 14 is threaded to accept a retention screw for the second stage of the implantation procedure. One embodiment may preferentially use the standard 4.0 mm size retention screw. Implant 10 may use the internal hex design standard in implant dentistry.

Conduit 16 may be configured so as to convey fluid 24 from the inlet opening 22 to outlet opening(s) 20. Conduit 16 may be formed so as to be coaxial with a central axis 18 of implant 10, and extend in a generally longitudinal direction of implant 10 from coronal end 14 towards apical end 12. Conduit 16 extends through the length of implant 10 with one or a plurality of outlet apertures 20 at the apical end 12 of implant 10, and an inlet/retention screw opening 22 at coronal end 14. Further, inlet opening 22, conduit 16, and apertures 20 are configured for implantation in a bone such that when fully implanted, inlet opening 22 remains open to receiving fluid bone-grafting material 24. Our exemplary embodiment includes a plurality of outlet openings 20, although certain embodiments may include only a single outlet opening 20. On the exterior of implant 10, the coronal portion 14 is self-tapping surgical grade titanium, while apical portion 12 is non-threaded.

Coronal end 14 of the implant 10 may be configured to permit a prosthesis to be connected thereto. For example, when implant 10 is configured for insertion in a maxillary or jaw bone 40, the coronal end 14 may be configured to support a prosthetic tooth. For other uses, differing prosthetics and other attachments may be connectable to coronal end 14 via mechanical, magnetic, or adhesive connection. Such connecting features may include, for example, internal hexagonal connections, external hexagonal connections, other anti-rotational connections, external screw threads, internal screw threads, lock nut constructions, friction fittings, bayonet type mounts, pin connectors, eyelets, or any other structure that permits secure mechanical connection to the implant 10. In one exemplary embodiment, we use the internal hex connection. It is understood that the invention is not limited to implants with particular connecting features.

A resorbable barrier membrane 28 surrounds the implant 10 such that the extrusion of fluid 24 through the outlet apertures 20 causes the membrane 28 to unfurl and hold the fluid 24 in place in close proximity to implant 10. Once the fluid bone-grafting material 24 is in place, it hardens in that location, which creates primary stability. The outlet apertures 20 open through the implant 10 itself, but are covered by the membrane 28. Membrane 28 may be any of a number of bioresorbable membranes known in the dental arts, including, but not limited to BioSorb™, Cytoplast™, or OsteoShield™.

Figure 4:
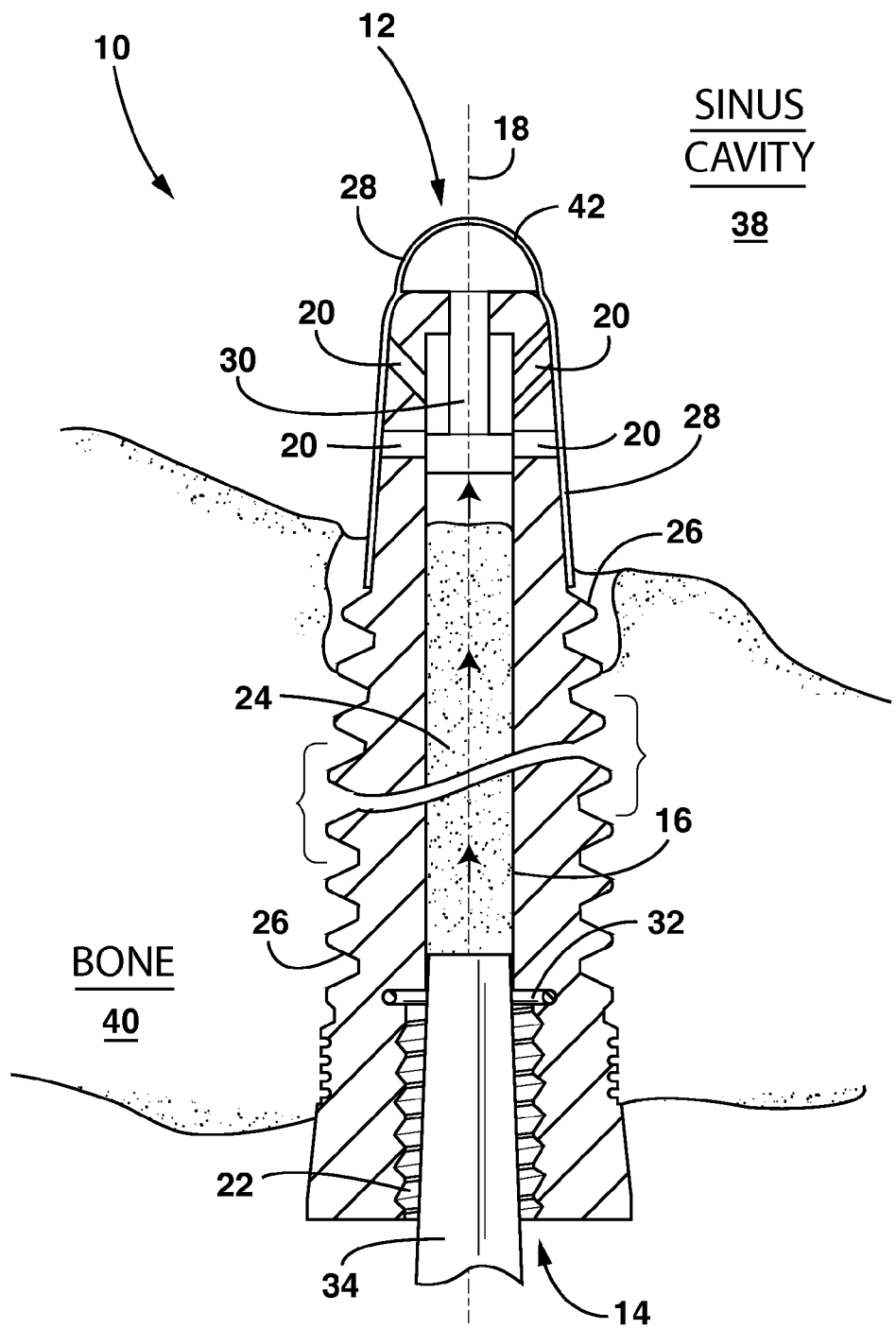
FIG. 4 is a section view of a dental implant being filled with biodegradable cement.
Figure 5:
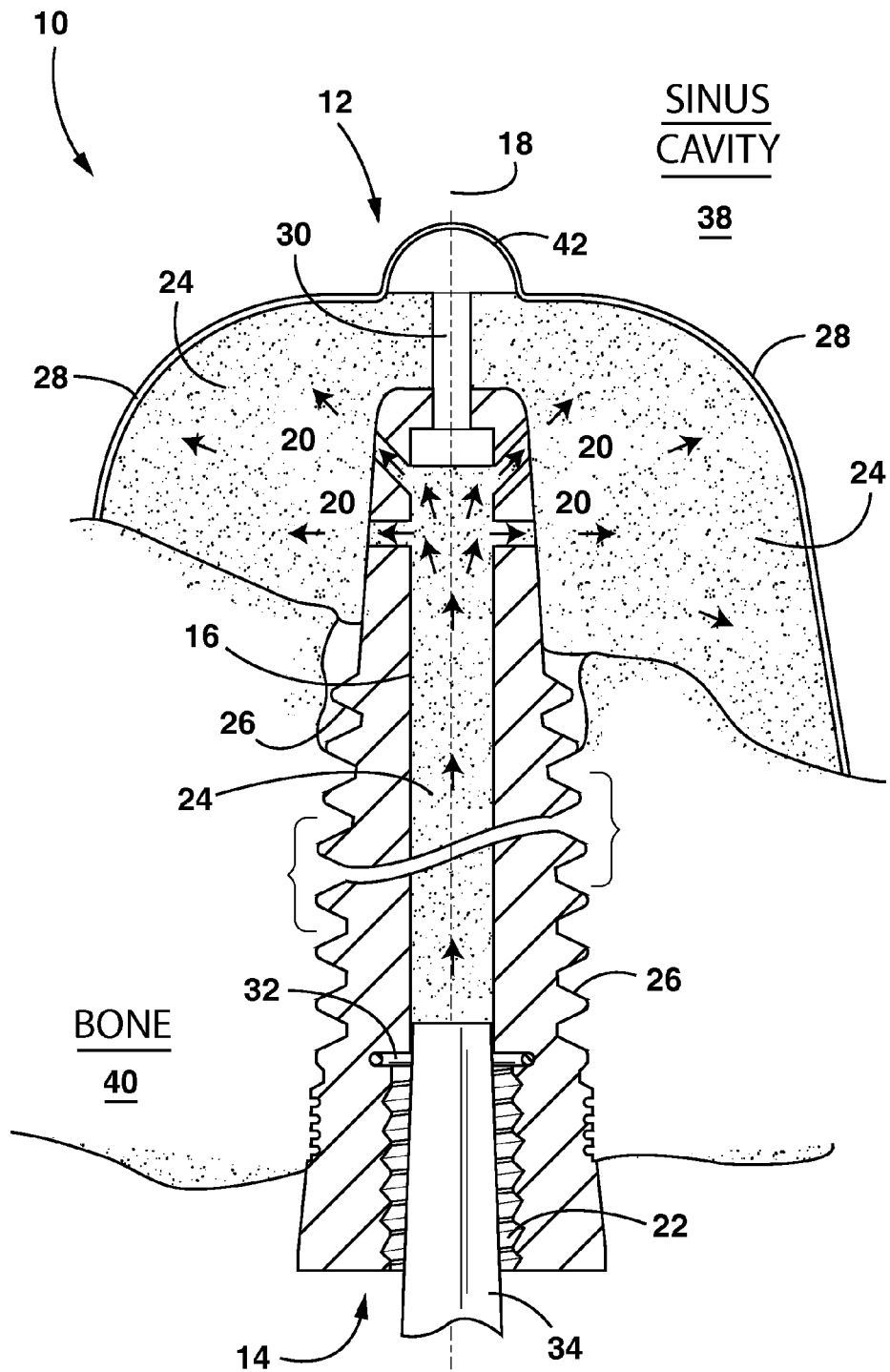
FIG. 5 is a section view with the resorbable barrier membrane unfurled.

A dowel pin 30 is provided within conduit 16, connected to the membrane 28, and configured to slide apically along the conduit 16 as bone-grafting material 24 is extruded, thereby aiding in the membrane 28 unfurling. The dowel pin 30 may be roughly dumbbell shaped. The resorbable barrier membrane 28 is connected via biodegradable cement 42 to the apical end 12 of dowel pin 30, and sits passively on the non-threaded apical portion 12 of the exterior of the implant 10. When dowel pin 30 slides out the apical end 12 of the implant 10, the membrane 28 opens up like an umbrella, holding the extruded bone-grafting material 24 close to the implant 10 while it hardens. FIGS. 4-5 demonstrate this extrusion and unfurling.

As used herein, "fluid," "fluid graft material," "liquefied graft material," or "fluid bone-grafting material" may refer to, by way of non-limiting example, any one of or a combination of saline solution, water, bone growth stimulation factors such as bone morphogenic protein (BMP), blood, bone graft, stem cell-based bone graft, bone regenerative material, bone augmenting material, an allograph, a xenograft, or any other flowable biocompatible material. Further, fluid may, for example, comprise a natural material, a synthetic material, or a mixture thereof For example, fluid may include one of the following commercially available fluid bone graft materials: DBX Paste (MTF), BioBone (Winsix), Ceramment (Bone Support), DynaGraft (Citagenix/ISOTIS), Fisiograft (Ghimas), Grafton DBM Gel (Osteotech), Optium DBM Gel (Lifenet/Depuy J&J), OsteoMax (Orthfix), PD VitalOs Cement (VitalOs), or Regenafil (Exactech). As is known in the art, once the fluid bone-grafting material 24 is in place, it hardens to create primary stability, acting as a scaffolding for the bone.

The graft material 24 is held in close physical proximity to the implant 10 by the membrane 28, thus creating bone stabilization. Exposure to bodily fluids will start the process of dissolving the unfurled membrane 28 and generating bone as in a conventional graft. The implant 10 should be configured for implantation into the bone 40 of a patient. When fully-implanted, the coronal inlet opening 22 should allow access to the conduit 16.

Any appropriate structure may be configured to aid in the insertion of implant 10 into the bone 40 of a patient including, for example, any appropriate electrical or mechanical tooling (e.g., a wrench, surgical screwing tool, etc.) which may be attached to the coronal end 14 of the implant. A surgical screwing tool may comprise a conventional manual ratchet wrench, or a conventional drill or motor to which an appropriate drill head is attached, and may be operated at a controlled speed and at controlled torque. Alternatively, any appropriate tool known in the art may be used to advance the implant 10 into the bone 40 of the patient.

Figure 3:
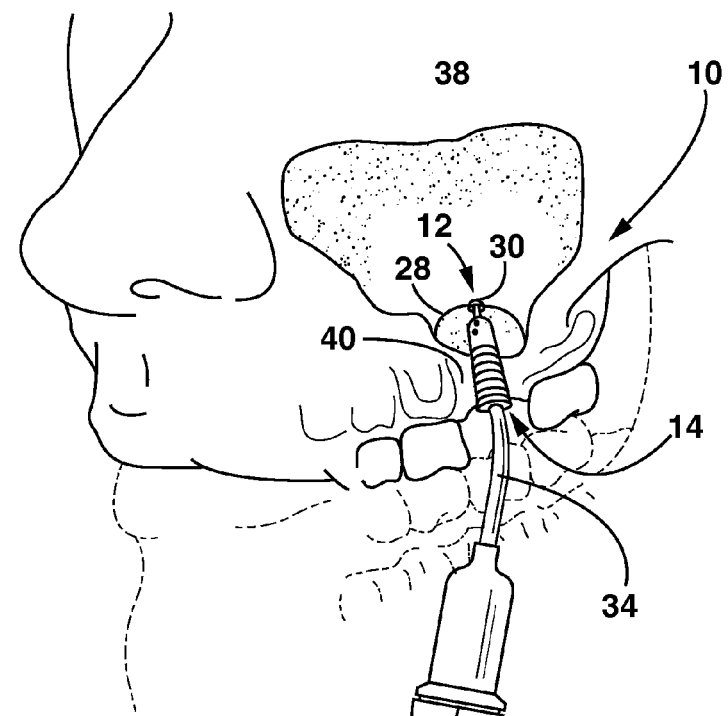
FIG. 3 is a view of the invention in use.
Figure 3:
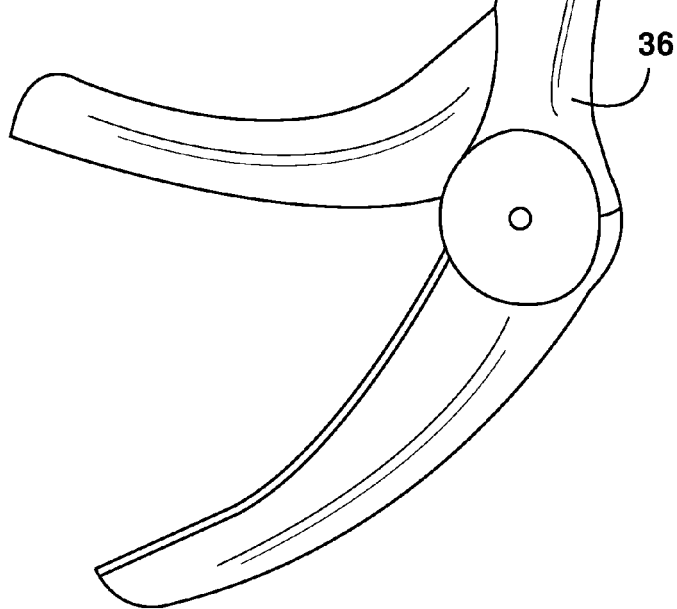

One embodiment of the present invention is a method for injecting fluid bone-grafting material 24 into dental implant 10. The inlet opening 22 may be connected to a container configured to store fluid 24 and may be of any shape or size appropriate to hold sufficient quantities of fluid 24 as may be dictated by the specific application. In one exemplary embodiment, the container is a compule gun 36. FIG. 3 demonstrates the use of the compule gun 36 to inject fluid 24 into the implant 10. Alternatively, the container may include any commercially available syringe or powered drug delivery device capable of delivering fluid into the conduit 16 through the coronal inlet opening 22. The fluid 24 may be injected using any appropriate means. For example, fluid 24 may be injected using a syringe, an LOR syringe, a powered drug delivery device, or any other known device for injecting fluid. As is known in the art, fluid 24, which, for example, can include regenerative material, may harden after injection, and induce bone growth in the area of injection.

The fluid 24 should not come into contact with the threads in the internal conduit 16. Thus, about 2 mms apically to the end of the implant 10 internal screw junction is a circumferential protrusion 32 (an O-ring). In one exemplary embodiment, the graft material compule tip 34 is pushed—past the O-ring protrusion 32—so that the dowel pin 30 slides out into its "open" position. At that point, the compule tip 34 is withdrawn until the dentist feels the O-ring protrusion 32. The liquefied bone grafting material 24 may then be manually injected into the implant 10 and out through the outlet apertures 20.

In the foregoing description, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this description, with each claim standing on its own as a separate embodiment of the invention.

Although the present invention has been described in considerable detail with reference to certain preferred versions thereof, other versions are possible. Therefore, the spirit and scope of the appended claims should not be limited to the description of the preferred versions contained therein.

The invention claimed is:

1. An apparatus, comprising:
   a dental implant, having an apical end and a coronal end, the implant shaped so as to define a conduit therethrough, having at least one aperture towards the apical end;
   a means for extruding fluid through the aperture or apertures;
   a membrane surrounding the apical end, configured to unfurl as fluid is extruded from the aperture or apertures; and
   a dowel pin connected to the membrane and configured to slide apically along the conduit so that fluid entering the conduit extrudes out the aperture(s).

2. The apparatus of claim 1 wherein the dental implant is made of self-tapping titanium.

3. The apparatus of claim 1 wherein the conduit further comprises an inlet at the coronal end of the dental implant.

4. The apparatus of claim 1 wherein the shape of the dental implant is approximately conical.

5. A method, comprising:
   providing a dental implant having an apical end and a corona' end. the implant shaped so as to define a conduit therethrough, having at least one aperture towards the apical end, a means for extruding fluid through the aperture or apertures, and a membrane surrounding the apical end, configured to unfurl as fluid is extruded from the aperture or apertures, and a dowel pin connected to the membrane and configured to slide apically along the conduit so that fluid entering the conduit extrudes out the aperture(s);
   drilling or boring a hole;
   inserting the implant into the hole; and
   injecting a fluid through the conduit.

6. The method of claim 5 wherein the dental implant is made of self-tapping titanium.

7. The method of claim 5 wherein the fluid is injected into the conduit via an inlet at the coronal end of the dental implant.

8. The method of claim 5 wherein the shape of the dental implant is approximately conical.

* * * * *